United States Patent [19]

Chohata et al.

[11] Patent Number: 5,155,751
[45] Date of Patent: Oct. 13, 1992

[54] SYSTEM FOR MAKING AN ON-LINE DETERMINATION OF DEGREE OF ALLOYING IN GALVANNEALED STEEL SHEETS

[75] Inventors: Kazuaki Chohata; Minoru Saito; Toshiharu Kittaka; Takeshi Nagatani; Yusuke Hirose, all of Sakai, Japan

[73] Assignee: Nisshin Steel Co., Ltd., Tokyo, Japan

[21] Appl. No.: 755,494

[22] Filed: Aug. 30, 1991

[30] Foreign Application Priority Data

Aug. 31, 1990 [JP] Japan ................................. 2-228185

[51] Int. Cl.⁵ .......................................... G01N 23/20
[52] U.S. Cl. ......................................... 378/71; 378/70
[58] Field of Search ..................... 378/70, 71, 74, 80, 378/79, 87, 88, 83, 89, 90, 62

[56] References Cited

FOREIGN PATENT DOCUMENTS

| 59-91343 | 9/1984 | Japan. |
| 62-135755 | 9/1984 | Japan. |
| 60-14109 | 6/1985 | Japan. |
| 63-301956 | 4/1989 | Japan. |

Primary Examiner—Constantine Hannaher
Assistant Examiner—Don Wong
Attorney, Agent, or Firm—Fleit, Jacobson, Cohn, Price, Holman & Stern

[57] ABSTRACT

A system for making an on-line determination of the degree of alloying in galvannealed steel sheets are provided, which includes an X-ray tube for generating X-ray, detectors for detecting the X-ray diffraction intensity of the $\zeta$ phase and $\Gamma$ phase of Fe—Zn intermetallic compounds phases of the galvannealed steel sheet and a detector for detecting the background intensity, all of the detectors being located same plane on the surface of the galvannealed steel sheets, and further includes an arithmetic unit for receiving the outputs of the detectors to compute the X-ray diffraction intensities. Preferably, this system includes a detector for detecting the X-ray diffraction intensity of the $\delta_1$ phase.

4 Claims, 6 Drawing Sheets

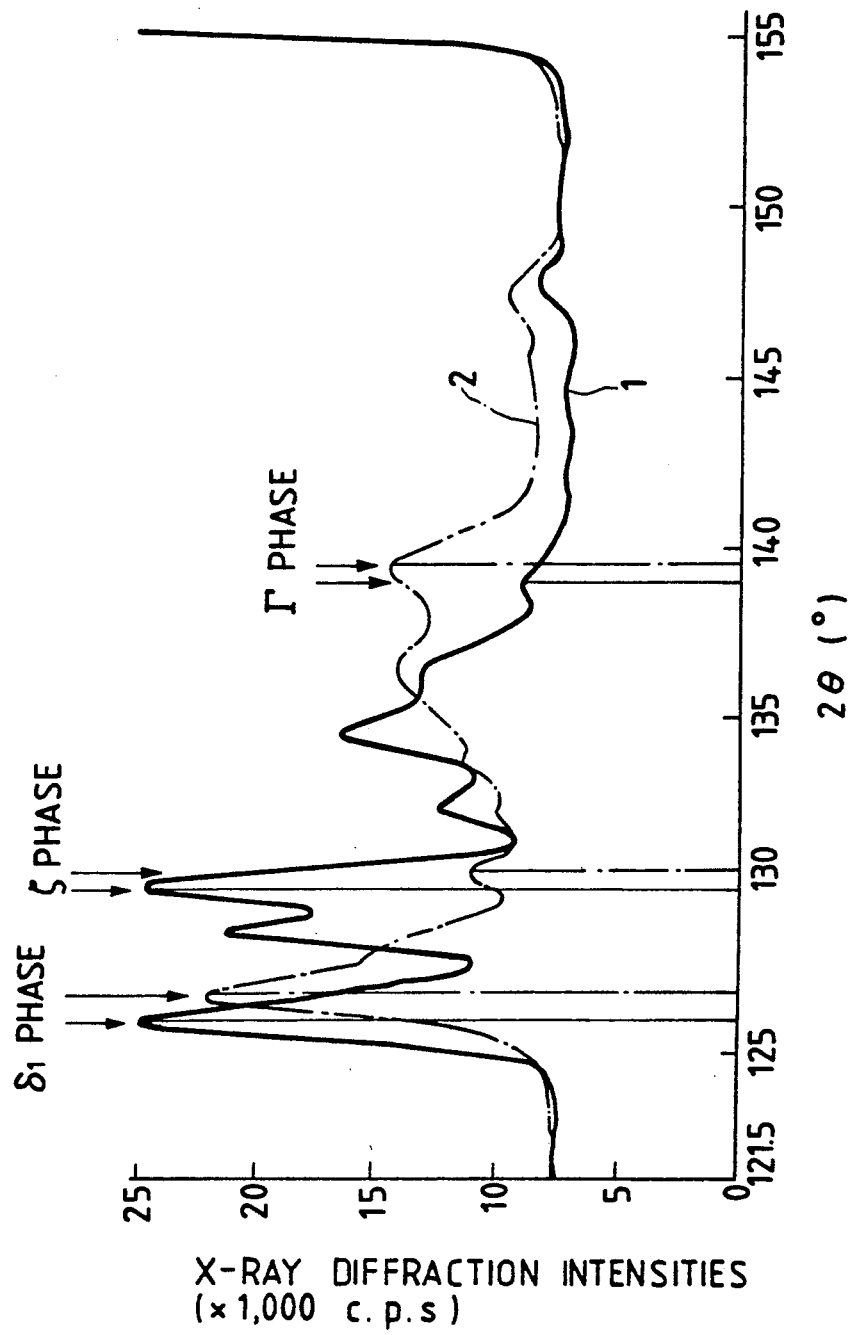

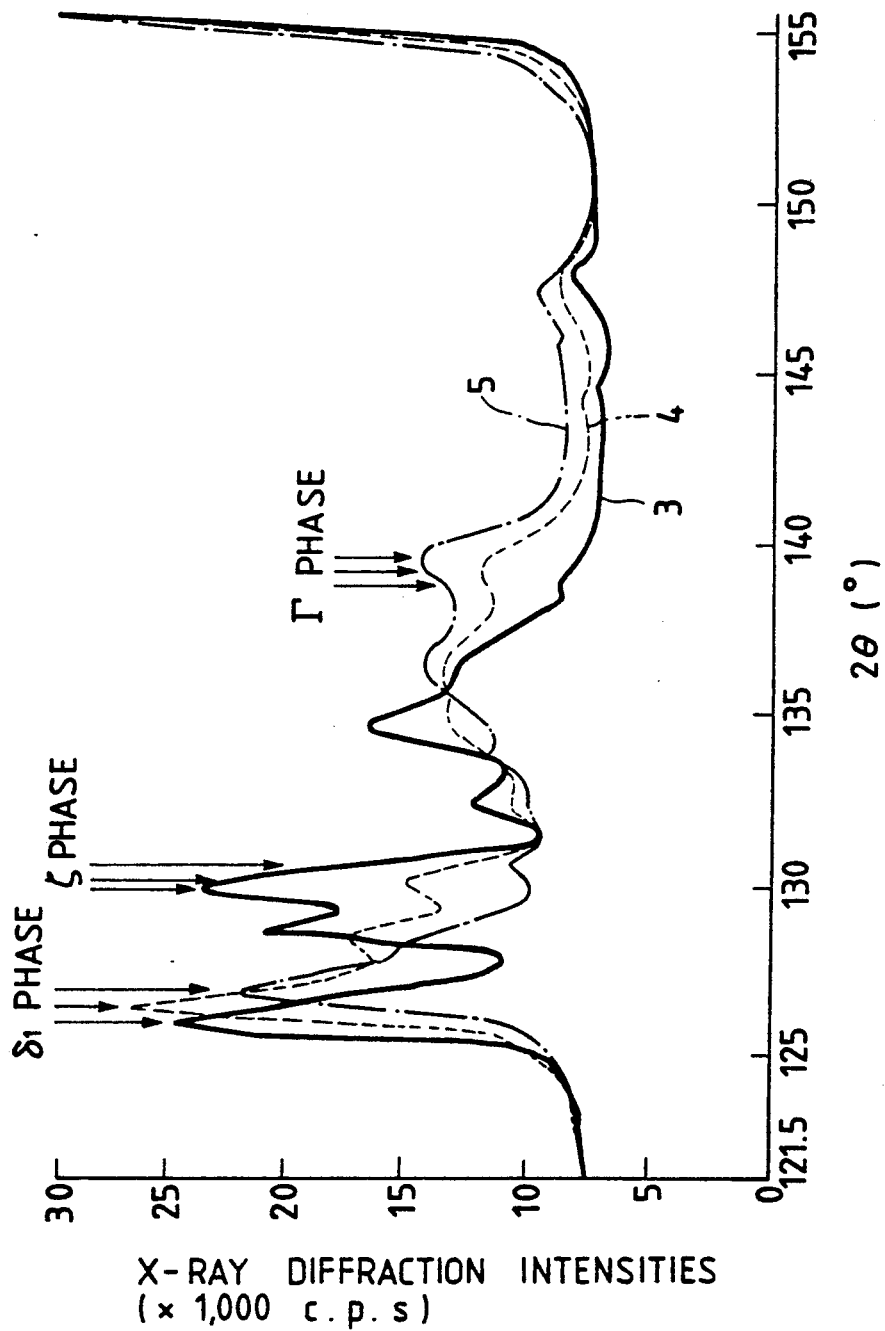

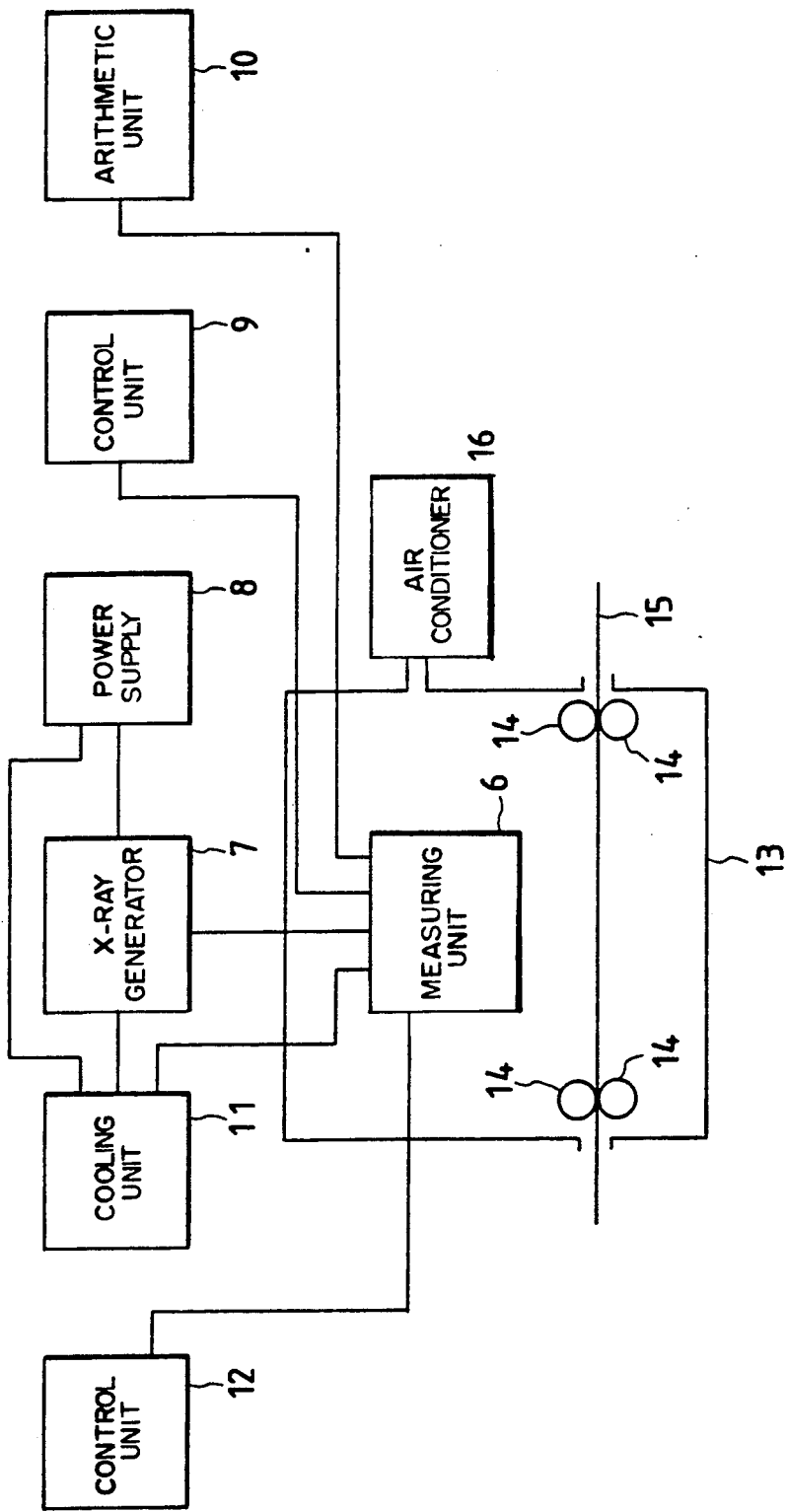

SYSTEM FOR MAKING AN ON-LINE DETERMINATION OF DEGREE OF ALLOYING IN GALVANNEALED STEEL SHEETS

BACKGROUND OF THE INVENTION

1. Field of the Invention

The present relates to a system for making an on-line, non-destructive and continuous determination of degree of alloying in galvannealed steel sheets with the use of X-ray diffractometry, said galvannealed steel sheets being produced by the application of heat treatments just following zinc coating.

2. Statement of the Prior Art

So far, galvannealed steel sheets—to which paintability, paint adhesion property and weldability are imparted in addition to the corrosion resistance of galvanized steel—have been produced with wide applications. This galvannealed steel sheets has been produced by subjecting steel sheets to a continuous process of hot-dip galvanizing, electro-galvanizing or zinc vapor depositing and then to post-heat treatments, thereby alloying the zinc coating and the base steel each other.

When the steel sheets are heat-treated after zinc coating in such a way as mentioned above, the $\eta$-Zn phase in coating layer is disappeared with the progress of alloying by diffusion of Fe and Zn, and the $\zeta$ (FeZn$_{13}$), $\delta_1$ (FeZn$_7$) and $\Gamma$ (Fe$_5$Zn$_{21}$) phases grow successively.

Heretofore, it has been said that the quality of the galvannealed steel sheets have a close correlation with the degree of alloying. When the degree of alloying is so low that a relatively soft, thick layer of the $\zeta$ phase remains on the surface of the coating layer, it is so increased in the surface friction with a mold (die) during press forming that its feeding into the mold gets worse, it is preferable to reduce the proportion of the $\zeta$ phase. In view of the paintability and cosmetic corrosion resistance of galvannealed coating thereon, however, the proportion of the $\zeta$ phase should preferably remained. When the degree of alloying is so high that a hard but brittle, thick layer of the $\Gamma$ phase grows between the coating layer and the base steel on the other hand, "powdering"—a phenomenon that the coating layer peels off the $\Gamma$ phase in powdery forms—takes place. If this powdering phenomenon occurs to some considerable extent, not only is press forming adversely affected, but the corrosion resistance of the galvannealed steel sheets become poor, because the coating layer disappears substantially, if not completely.

In order to produce an galvannealed steel sheets having improved quality, it is thus required to control the degree of alloying, whereby the growth of the $\Gamma$ phase is controlled to permit an appropriate proportion of the $\zeta$ phase to remain on the surface of the coating layer.

For determining of the degree of alloying of galvannealed steel sheets, various methods have been used so far in the art, as mentioned below.

The simplest method of all involves a visual or photometric determination of a hue change in the surface of the coating layer just following galvannealing or a visual determination of the amount of the coating layer peeled from a sample by a bending/bending-back test—the so-called powdering test, but it is inaccuracy. There is also available a chemical analysis of the average content of Fe in the coating layer of a test piece, which has conventionally been used as an index to the degree of alloying. However, a problem with this chemical determination is that it takes much time from sampling to the completion of analysis, incurring some time lag in feeding the output back to heat-treating in alloying furnace.

In order to determine the degree of alloying from the structure of a coating layer, to this end, a sample may be polished in cross-section to observe the cross-section of the coating layer under an optical microscope or a scanning electron microscope etc, thereby measuring the thicknesses of the $\zeta$, $\delta_1$ and $\Gamma$ phases. Alternatively, a sample may be measured for its X-ray diffraction profiles with an analytical X-ray diffractometry device, whereby the degree of alloying is determined with the X-ray diffraction intensities of the $\zeta$, $\delta_1$ and $\Gamma$ phases. These methods are preferable in a sense of providing a determination of the degree of alloying from the structure of the coating layer. However, a problem in these methods is that it takes much time from sampling to the completion of analysis, incurring some time lag in feeding the output back to heat-treating in alloying furnace. A problem common to all the above-mentioned powdering test, chemical analysis, cross-sectional observation and X-ray diffractometric analysis is that because of their destructive examination, it is impossible to provide a determination of the degree of alloying of galvannealed steel sheets along the entire widthwise or line direction.

On the other hand, X-ray diffractometric methods have been proposed to make an on-line, non-destructive and continuous determination of the degree of alloying. For instance, Japanese Patent Laid-Open No. 61-148355 discloses a method for determining the average content of Fe in a coating layer by measuring the X-ray diffraction intensities of the $\Gamma$ phase with a interplanar spacing of d=approx. 1.22 Å and the $\alpha$-Fe phase with a interplanar spacing of d=approx. 1.44 Å and substituting the two measurements for a functional equation for the average content of Fe in the coating layer, using as the variables the pre-calculated X-ray diffraction intensities of the $\alpha$-Fe and $\Gamma$ phases. With this method in which what is measured is limited to the $\Gamma$ phase, it is impossible to measure the amounts of the $\zeta$ and $\delta_1$ phases formed and find the structure of the coating layer accurately.

With these conventional methods for determining the degree of alloying by X-ray diffractometry, it is also impossible to measure X-ray diffraction intensities accurately, because the detector for diffracted X-rays is fixed at a $2\theta$ position (diffraction angle) of a specific lattice plane of the Fe-Zn intermetallic compound phases to be measured. In other words, the $\zeta$, $\delta_1$ and $\Gamma$ phases are all non-stoichiometric compounds that vary in the content of Fe depending upon the degrees of diffusion of Fe and Zn, as can be seen from an equilibrium state phase diagram on which the $\zeta$ phase has an Fe content range of about 5.5 wt. % to about 6.2 wt. %, the $\delta_1$ phase has an Fe content range of about 7.0 wt. % to 11.4 wt. % and the $\Gamma$ phase has a Fe content range of about 20.0 wt. % to about 28.0 wt. %. Depending upon the degree of alloying, there are thus changes in the interplanar spacing of the $\zeta$, $\delta_1$ and $\Gamma$ phases and consequently results in the change of the $2\theta$ positions of the X-ray diffraction peaks of the respective phases. This phenomenon—which has been experimentally confirmed by inventors of the present invention—will now be explained more illustratively with reference to FIG. 1 showing the X-ray diffraction profiles of galvannealed coating, each with a coating weight of about 45 g/m$^2$, which have been heat-treated in salt bath at 500° c. for 5 seconds and 60 seconds for alloying, with the use of a Cr tube (operating at a tube voltage of 40 kV and a tube current of 70 mA). In FIG. 1, reference numeral 1 represents for the X-ray diffraction profile of the galvannealed coating prepared by a 5-second heat-treatment at 500° c. and 2 stands for that of the galvannealed coating prepared by a 60-second heat-treatment at 500° c. As can be understood from FIG. 1, the apex positions of the X-ray diffraction peaks of the $\zeta$, $\delta_1$ and $\Gamma$ phases of the galvannealed coating heated at 500° c. for 5 seconds lie at $2\theta = 130.0°$, $2\theta = 126.0°$ and $2\theta = 139.0°$, respectively, but those of the galvannealed coating having an increased degree of alloying because of having been heated at 500° c. for 60 seconds are found at somewhat higher levels, say, $2\theta = 130.5°$, $2\theta = 127.0°$ and $2\theta = 139.5°$, respectively. As an example, now assuming that the degree of alloying is measured at the X-ray diffraction intensity of the $\delta_1$ phase having a interplanar spacing of d=approx. 1.28 Å, it is then noted that with a diffracted X-ray detector fixed at the apex position of the X-ray diffraction peak of the $\delta_1$ phase of the galvannealed coating heated at 500° c. for 5 seconds, say, $2\theta = 126.0°$, the X-ray diffraction intensity of the $\delta_1$ phase of the galvannealed coating—having an increased degree of alloying because of having been heated at 500° c. for 60 seconds—is measured to be about 14,000 (c.p.s.) at this position. In other words, the measurement is in error by as much as about 8,000 (c.p.s.), because the peak apex position of the latter galvannealed coating lies at $1\theta = 127.0°$ where the X-ray diffraction intensity is about 22,000 (c.p.s.). Therefore, when the diffracted X-ray detector is fixedly located at the $2\theta$ position of a specific lattice plane, the peak apex position changes with a change in the degree of alloying, deviating from that detector and so rendering it unable to measure the X-ray diffraction intensity, i.e. the degree of alloying, constantly and normally.

As already stated, the $\zeta$, $\delta_1$ and $\Gamma$ phases are all non-stoichiometric compounds, each having a certain range of Fe content. Although depending upon the alloying conditions applied and the type of base steel to be coating, this gives rise to changes in the contents of Fe of the $\zeta$, $\delta_1$ and $\Gamma$ phases and, in turn, causes the average content of Fe to vary throughout the coating layer, even though the $\zeta$, $\delta_1$ and $\Gamma$ phases are formed in the same quantities. Thus, it is unfeasible to provide an accurate determination of the average content of Fe in a coating layer by X-ray diffractometry.

As explained above, the X-ray diffractometric methods may be effective for an on-line, non-destructive and continuous determination of the degree of alloying. With the conventional methods wherein, as stated above, the diffracted X-ray detector is fixedly located at the $2\theta$ position of the specific lattice plane of interest, however, it is impossible to measure the X-ray diffraction intensity constantly at the apex position of the X-ray diffraction peak, only to reduce the accuracy of measurement, and to get information of amounts of formation of the $\zeta$, $\delta_1$ and $\Gamma$ phases or the structure of the coating layer.

An accurate determination of an X-ray diffraction intensity at the apex location of an X-ray diffraction peak may be achieved by measuring the associated X-ray diffraction profile. To this end, the X-ray diffraction profile is conventionally measured by scanning one detector with respect to an X-ray tube within a certain $2\theta$ range according to the $\theta - 2\theta$ scanning method.

However, if it is intended to make an on-line determination of the X-ray diffraction, much time is then needed for detector scanning, during which the degree of alloying will vary, making it unable to measure the X-ray diffraction profile correctly.

The present invention seeks to solve the above-mentioned problems of the prior art by the provision of a system for making an on-line, non-destructive, continuous and accurate determination of the degree of alloying in galvannealed steel sheets.

When galvanized steel sheets are heat-treated for alloying, the $\zeta$, $\delta_1$ and $\Gamma$ phases are successively formed in the coating layer, as already referred to. And with the progress of alloying, the $\zeta$ phase disappears but, instead, the $\Gamma$ phase grows thickly. These phenomena are illustrated in FIG. 2 with reference to the X-ray diffraction profiles measured by X-ray diffractometry, and are schematically shown in FIG. 3 as well. The three curves shown in FIG. 2 represents the X-ray diffraction profiles of galvannealed coating, each having a coating weight about 45 g/m², which have been heat-treated on an salt bath for alloying. The curve 3 stands for the X-ray diffraction profile of the galvannealed coating which has been heat-treated at 500° c. for 5 seconds for alloying, and the structure of the coating layer thereof is schematically sketched in FIG. 3a. The curve 4 explains the X-ray diffraction profile of the galvannealed coating which has been heat-treated at 500° c. for 30 seconds for alloying, and the structure of the coating layer thereof is schematically depicted in FIG. 3b. The curve 5 shows the X-ray diffraction profile of the galvannealed coating which has been heat-treated at 500° c. for 60 seconds for alloying, and the structure of the coating layer thereof is schematically sketched in FIG. 3c. With further reference to FIGS. 2 and 3, the longer the heat-treatment time and the more the degree of alloying, the smaller the volumetric proportion of the $\zeta$ phase and the lower the X-ray diffraction intensity. By contrast, however, an increase in the volumetric porportion of the $\Gamma$ phase results in an increase in the X-ray diffraction intensity. The X-ray diffraction intensity of the $\delta_1$ phase increases, as the heat-treatment time increases from 5 seconds to 30 seconds, but decreases from 60 seconds after the heat-treatment. This is because with the progress of alloying. The volumetric proportion of the $\zeta$ phase decreases with an increase in the volumetric proportion of the $\delta_1$ phase; however, the continued progress of alloying causes a decrease in the volumetric proportion of the $\delta_1$ phase due to an increase in the volumetric proportion of the $\Gamma$ phase.

In addition, as the degree of alloying increases with an increase in the heat-treating time, the apex locations of the X-ray diffraction peaks of all the $\zeta$, $\delta_1$ and $\Gamma$ phases are shifted toward somewhat higher $2\theta$ position.

SUMMARY OF THE INVENTION

With these phenomena in mind, the inventors have accomplished an X-ray diffraction system for achieving an on-line, non-destructive, continuous and accurate determination of the degree of alloying of galvannealed steel sheets from the X-ray diffraction intensities of the $\zeta$ and $\Gamma$ phases, and preferably the $\delta_1$ phase—which vary with a change in the degree of alloying—at the apex positions of the X-ray diffraction peaks.

BRIEF DESCRIPTION OF THE DRAWINGS

The above-mentioned and other objects and features of this invention and the manner of attaining them will become apparent, and the invention itself will be best understood by reference to the following description of the embodiment of the invention in conjunction with the accompanying drawings, wherein:

FIG. 1 is a diagram showing the X-ray diffraction profiles of hot-dip galvannealed coating—each coating weight of about 45 g/m$^2$—which have been heat-treated on a salt bath at 500° c. for 5 seconds and 60 seconds, FIG. 2 is a diagram showing the X-ray diffraction profiles of hot-dip galvannealed coating—each coating weight of about 45 g/m$^2$—which have been heat-treated on a salt bath at 500° c. for 5 seconds, 30 seconds and 60 seconds, FIGS. 3(a), (b) and (c) are schematic sketches illustrating the structures of the coating layers corresponding to the three X-ray diffraction profiles of FIG. 2, FIG. 4 is a schematic view of one embodiment of the system according to this invention.

ILLUSTRATIVE EXPLANATION OF THE INVENTION

Figure 3A:
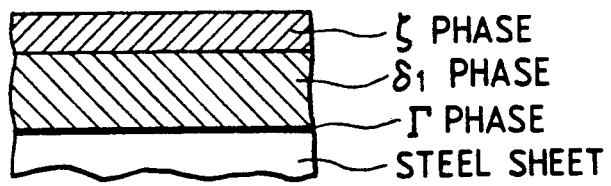
Figure 3B:
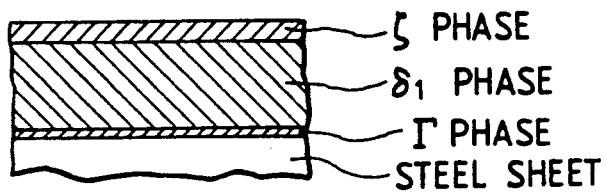
Figure 3C:
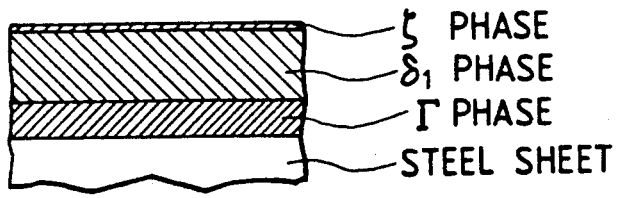

The present invention will now be explained more illustratively with reference to FIGS. 4-8.

Referring first to FIG. 4, there is schematically shown an embodiment of the inventive system for making an on-line determination of the degree of alloying in galvannealed steel sheets. As illustrated, the system according to this invention is built up of a measuring unit 6, an X-ray generator 7, a high-voltage powder supply 8, a control unit 9 for controlling the operation of the X-ray generator and detector scanning, an arithmetic unit 10 for receiving the calculation reasults of the X-ray diffraction intensity obtained by the associated detectors, a cooling unit 11 for cooling an X-ray tube etc, a control unit 12 for traversing the measuring unit in widthwise direction of the galvannealed steel sheet, a chamber 13 for shielding X-rays, and two pairs pinch rolls 14 for preventing fluctuations of the galvannealed steel sheet and a leakage of X-rays. The galvannealed steel sheet is shown at 15. The measuring unit 6 is designed to be traversed in the widthwise direction of the galvannealed steel sheet 15 through a traverse equipment, not shown. The shielding chamber 13 is controlled at a constant internal temperature by an air conditioner 16. This is because a change in the internal temperature of the chamber 13 gives rise to a change in air density, which otherwise leads to a change in the absorption of X-rays by air and a deterioration of the accuracy of measurement.

Figure 5:
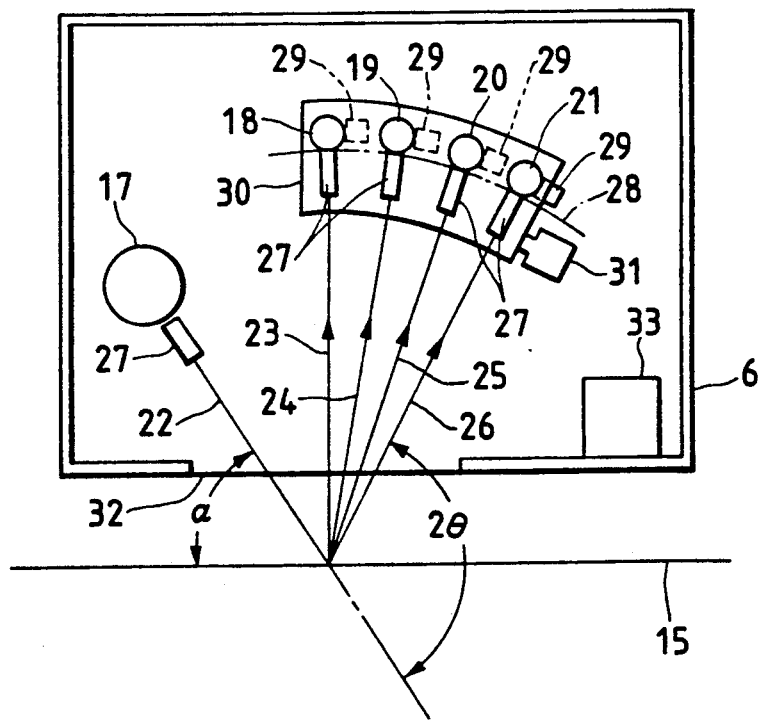
FIG. 5 is a schematic view of the internal structure of the measuring unit.

Referring now to FIG. 5—a schematic sketch illustrating the internal structure of the measuring unit 6 used with the present system, reference numeral 17 represents an X-ray tube for generating X-ray, 18 a detector for measuring the background intensity, 19 a detector for measuring the X-ray diffraction intensity of a Γ phase, 20 a detector for measuring the X-ray diffraction intensity of a ζ phase, 21 a detector for measuring the X-ray diffraction intensity of a δ$_1$ phase, 22 incident X-rays, 23, 24, 25 and 26 diffracted X-rays from the background, Γ, ζ and δ$_1$ phases, 27 a solar slit, and 28 a scanning circle whose center is defined by the point of intersection of the incident X-ray 22 with the galvannealed steel sheet 15 and the radius defined by the distance between the center and each detector 18, 19, 20 or 21. The detectors 18-21 (including the solar slits 27) are each provided with a driving motor 29. In addition, they are mounted on a common scanning plate 30 together with the associated motors 29, which is also provided with a driving motor 31. The detectors 18-21 (including the solar slits 27) can be independently or simultaneously driven on the scanning circle 28 by the motors 29 for scanning purposes. More illustratively, they can be simultaneously driven on the scanning circle 28 by driving the scanning plate 30 with the motors 29. Reference numeral 32 stands for a window formed as of a polyimide film. In order to prevent corrosion of the X-ray tube 17, etc., a certain amount of a low-humidity air or an inert gas such as nitrogen gas is fed as an atmospheric gas into the measuring unit 6 and removed therefrom. Also, the inside of measuring unit 6 is regulated to a constant temperature by a temperature control unit 33. This is because a temperature change in the atmospheric gas brings about a density change in the atmospheric gas, which otherwise results in a change in the absorption of the incident X-rays and the diffracted X-rays 23-26 by the atmospheric gas, i.e., deterioration of the accuracy with which the X-ray diffraction intensities can be measured.

In the present system, the X-ray tube 17 and detectors 18-21 (including the solar slits 27) are located same plane on the surface of the galvannealed steel sheet, which meets the Bragg's formula represented by the following equation:

$$n\lambda = 2d \sin \theta$$

wherein:
n is the index of reflection,
λ is the wavelength of the X-ray (Å),
d is the interplanar spacing (Å), and
θ is the Bragg angle (the diffraction angle of X-ray) (degree).

For scanning purposes, the detectors 18-21 (including the solar slits 27) are then independently or simultaneously driven within the ranges of the following interplanar spacing d of lattice planes on the scanning circle 28 with the center located at the point of intersection of the incident X-ray 22 with the galvannealed steel sheet 15.

Scanning ranges of the detectors is shown in as follows.

For the detector for measuring the X-ray diffraction intensity of the ζ phase: the interplanar spacing d of lattice planes = 1.30Å–1.23Å;

For the detector for measuring the X-ray diffraction intensity of the δ$_1$ phase: the interplanar spacing d of lattice planes = 1.32Å–1.25Å;

For the detector for measuring the X-ray diffraction planes of the Γ phase: the interplanar spacing d of lattice planes = 1.25Å–1.20Å; and For the detector for measuring the background intensity: the interplanar spacing d of lattice planes = 1.20Å–1.17Å.

The interplanar spacing d of lattice planes of the $\zeta$, $\delta_1$ and $\Gamma$ phases to be measured with the present system are as follows:

d = approx. 1.26 Å for the $\zeta$ phase;
d = approx. 1.28 Å for the $\delta_1$ phase; and
d = approx. 1.22 Å for the $\Gamma$ phase.

While the X-ray diffraction peaks in the case of interplanar spacing larger than the above-defined spacings, i.e., those of the $\zeta$, $\delta_1$ and $\Gamma$ phases on somewhat lower $2\theta$ position have strong X-ray diffraction intensities, difficulty is involved in separating the peaks from each other due to their overlapping each other. In order to measure the degree of alloying with high accuracy, in other words, while limiting the influence, on the accuracy of the X-ray diffraction intensities to be measured, of a deviation of the galvannealed steel sheet 15 from the detectors 18–21 for the diffracted X-rays 23–26 due to its fluctuations, it is preferable to increase the angles $2\theta$ of exit of the diffracted X rays 23–26. This is the reason that the interplanar spacing d of lattice planes of the $\zeta$, $\delta_1$ and $\Gamma$ phases to be measured are fixed at the above-mentioned values at which the X-ray diffraction peaks do not overlap each other at all and the diffraction angles $2\theta$ of X-rays are increased. The interplanar spacing of lattice planes at the background-measuring position is also fixed at the above-defined value at which no X-ray diffraction peak is found.

Not all of the detectors 18–21 (including the solar slits 27) need be driven on the same scanning circle for scanning purposes. Where the scanning circle 28 varies in radius from place to place; the distances between the galvannealed steel sheet 15 and the detectors 18–21 vary, however, they must be corrected for intensity because of a difference in the X-ray diffraction intensities. It is thus preferred that the detectors 18–21 be driven on the same scanning circuit 28 for scanning purposes.

According to the inventive system, it is noted that the detectors 18–21 may be fixed in place within the above-mentioned scanning range to measure the degree of alloying.

The system for measuring X-ray diffraction intensities according to this invention operates in a stepwise scanning method wherein the detectors 18–21 are driven stepwise every minute angle within the above-mentioned range over a certain measuring span of time.

The measuring conditions are:
Step Angle: 0.01° to 1.00°, and
Measuring Time: 1 to 100 seconds.

Although the type of the X-ray tube 17 used with the present inventive system is not critical, the X-ray incidence angle $\alpha$ and the diffraction angle $2\theta$ thereof should preferably be enough large to prevent a deterioration in the accuracy of measurement by a deviation of the diffracted X-rays 23–26 form the detectors 18–21 due to fluctuations of the galvannealed steel sheet 15. Thus, it is preferable to use as the X-ray tube 17 a Cr tube generating a long wavelength and giving an increased angle $2\theta$. As the X-ray incidence angle $\alpha$ increases, the distance of transmission of the incident X-rays 22 through the coating layer becomes short, but the distance of transmission of the diffracted X-rays 23–26 becomes long; the absorption of the diffracted X-rays 23–26 by the coating layer increases, resulting in a decrease in the X-ray diffraction intensities and hence a deterioration in the accuracy of measurement. By contrast, as the X-ray incidence angle $\alpha$ decreases, the distance of transmission of the diffracted X-rays 23–26 decreases, but the distance of transmission of the incident X-rays 22 increases; the absorption of the incident X-rays by the coating layer increases, resulting in a decrease in the X-ray diffraction intensities and hence a deterioration in the accuracy of measurement. As a result of investigations made by the present inventors with a Cr tube, it has been found that the X-ray incidence angle $\alpha$ preferably lies in the range of 60° to 75°, at which the highest X-ray diffraction intensities are obtained.

While no particular limitation is placed on the optical system used, it is noted that a parallel beam type of optical system is preferable to a convergent beam type of optical system so as to limit the influence, on the accuracy of measurement of the X-ray diffraction intensities, of a deviation of the diffracted X-rays 23–26 from the detectors 18–21 by fluctuations of the galvannealed steel sheet 15.

The degree of alloying, i.e, the quality of galvannealed steel sheets may be determined in terms of the X-ray diffraction intensities found from the measured X-ray diffraction profiles at the apex positions of the X-ray diffraction peaks of the respective phases. In this case however, the X-ray diffraction intensities must be corrected in view of the coating weight, because they vary depending upon the coating weight, even though the degree of alloying is on the same level. For this reason, another extra equipment for measuring the coating weight is needed, not only incurring some considerable expense for obtaining the equipment but also rendering computing complicated.

Among the quality of the galvannealed steel sheet 15, of interest are the amounts of the $\zeta$ and $\Gamma$ phases formed, and the following two values for estimation are preferably used, with which the degree of alloying can be accurately found from the X-ray diffraction and background intensities of these two phases through a simple arithmetic operation, as set forth in specification of Japanese Patent Application No. 1-308917.

For estimation of the $\zeta$ phase:

$$\frac{I(\zeta) - I_B(\zeta)}{I(\zeta)}$$

For estimation of the $\Gamma$ phase:

$$\frac{I(\Gamma) - I_B(\Gamma)}{I(\Gamma)}$$

wherein:

$I(\zeta)$ is the total X-ray diffraction intensity of the $\zeta$ phase with a interplanar spacing d = approx. 1.26 Å (c.p.s.), $I(\zeta)$ is the total X-ray diffraction intensity of the $\zeta$ phase with a interplanar spacing d = approx. 1.28 Å (c.p.s.), and $I_B(\zeta)$ and $I_B(\zeta)$ are the background intensities of the X-ray diffraction peaks of the $\zeta$ and $\Gamma$ phases. In the present system, however, the X-ray diffraction intensity at a interplanar spacing of d = approx. 1.18 Å—at which no X-ray diffraction peak is found—is used expediently.

In addition, it is preferred that the accuracy of measurement of the degree of alloying can be much more improved by using, in combination with the above-mentioned values for estimation, the following value for estimation in which the X-ray diffraction and background intensities of the $\zeta$ and $\delta_1$ phases are used, as disclosed in Japanese Patent Laid-Open No. 56-12314.

$$\frac{I(\zeta) - I_B(\zeta)}{I(\delta_1) - I_B(\delta_1)}$$

By operating the present system, using the former two values for estimation, preferably along with the latter value for estimation, it is possible to make an on-line determination of the quality of the galvannealed steel sheet 15, especially, powdering property and drawing property—which are now taken as a serious problem—as well as press formability.

According to the system of the present invention wherein, as mentioned above, the detectors 18-21 are independently provided for detecting the X-ray diffraction and background intensities of the $\zeta$ and $\Gamma$ phases and, more preferably, for detecting the X-ray diffraction intensity of the $\delta_1$ phase and are driven within the above-mentioned range for scanning purposes, an on-line, continuous determination of the X-ray diffraction profiles within the interplanar spacing range of approx. 1.30 Å to 1.17 Å can be achieved within a short measuring time. In addition, it is possible to make an accurate determination of the X-ray diffraction intensities of the respective phases, even when the apex positions of the X-ray diffraction peaks vary with a change in the degree of alloying. It is thus possible to make an on-line, continuous determination of the quality of the galvannealed steel sheet 15 with improved accuracy. It is noted that for measuring the estimating values of the $\zeta$ and $\Gamma$ phases, only the detectors for measuring the X-ray diffraction intensities of the $\zeta$ and $\Gamma$ phases need be driven to effect scanning.

The system according to the present invention is applicable not only to the galvannealed steel sheet 15 produced by hot dipping method but also to all types of galvannealed steel sheets obtained by electro-galvanizing and zinc vapor deposition, just following by heat-treatments.

EXAMPLES

With the present system shown in FIGS. 4 and 5, the degree of alloying of galvannealed steel sheet was determined on a hot-dip galvanizing line of non-oxidizing furnace type.

The conditions for measuring the degree of alloying and for producing galvannealed steel sheets are mentioned below.

Conditions for measuring the degree of alloying:
X-ray tube: Cr target (with a wavelength Cr-k$\alpha_1$ of approx. 2.29 Å)
Optical system: parallel beam type.
Tube voltage: 40 kV
Tube current: 70 mA
Filter: No filter for the X-ray tube side; V for the side of detecting the intensities of the $\zeta$, $\delta_1$ and $\Gamma$ phases as well as the side of the background
Solar slit: 0.6°
X-ray incidence angle: 60°
Areas exposed to X-ray: 650 mm² (width: 10 mm, length: 65 mm)
Detectors: sealed type proportional counters.
Scanning ranges of the detectors wherein d is the interplanar spacing:

Detector for measuring the X-ray diffraction intensity of the $\delta_1$ phase: d=1.32Å-1.25Å (and $2\theta$=120.5-132.5°)
Detector for measuring the X-ray diffraction intensity of the $\zeta$ phase: d=1.30Å-1.23Å (and $2\theta$=124.3-136.3°).
Detector for measuring the X-ray diffraction intensity of the $\Gamma$ phase: d=1.25Å-1.20Å (and $2\theta$=133.0-145.0°).
Detector for measuring the background intensity: d=1.25Å-1.17Å (and $2\theta$=144.5°-156.5°)
Distance between the X-ray tube and galvannealed steel sheet: 300 mm
Distance between the galvannealed steel sheet and each detector: 500 mm
Atmospheric gas prevailing in the measuring head: dry air (with a dew point of −10° c. and at flow rate of 10 l/min.)
Internal temperature of the shielding chamber: 25° c.
Measuring method: Stepwise scanning
Step angle: 0.2°
measuring time: 1 second
For traversing the measuring head: the head is repeatedly reciprocated once per minute in the widthwise direction to measure three points on the galvannealed steel sheet, i.e., both sides of widthwise direction and the center, every one way.
Galvannealing conditions:
Type of base steel: Ti-added steel (C: 0.002%, Ti: 0.07%, Si: 0.15% and Mn: 0.13%)
Size of base steel: thickness: 0.7 mm and width: 1,000 mm
Zinc bath composition: 0.14 wt. % Al-Zn
Zinc bath temperature: 480° c.
Line speed: 50-150 m/min.
Base steel temperature in the galvannealing furnace: 480°-600° c.
Coating weight: approx. 30-60 g/m² (by gas wiping method)

It is noted that for the galvannealed, use was made of a galvannealed furnace including a plurality of direct flame type burners at positions from the edge to center of each side of the st eel sheet to be treated, while the amounts of gas fed to the burners were independently regulated.

Figure 6:
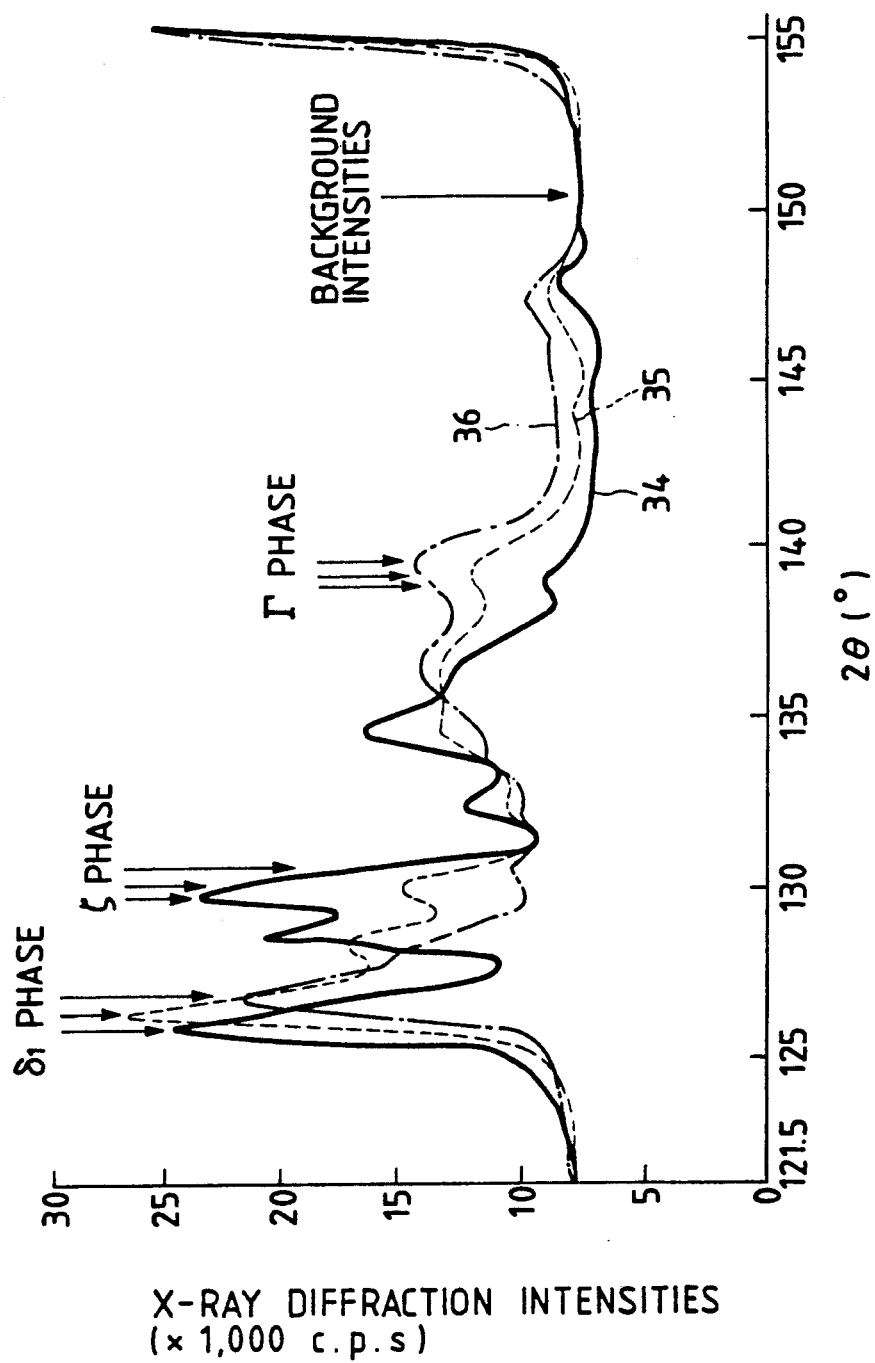
FIG. 6 is a diagram showing the X-ray diffraction profiles of hot-dip galvannealed coating—each comprising galvannealed steel sheets produced through a continuous galvannealing production line at a line speed of 100 m/min. and having a coating weight of about 45 g/m$^2$—which have been heat-treated at the respective alloying temperatures of 480° c., 520° c. and 600° c. in an galvannealing furnace.
Figure 7:
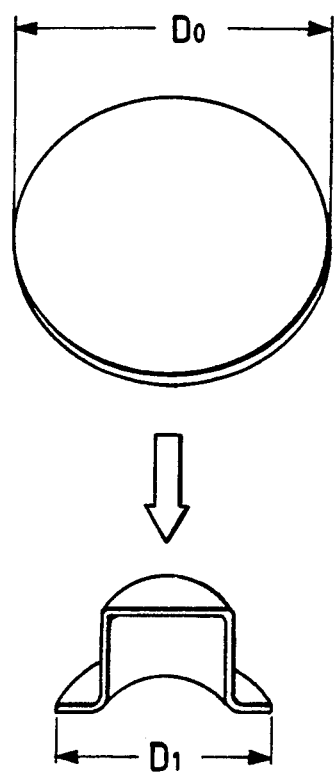
FIG. 7 is a diagrammatical sketch illustrating how to test a drawing property.
Figure 8:
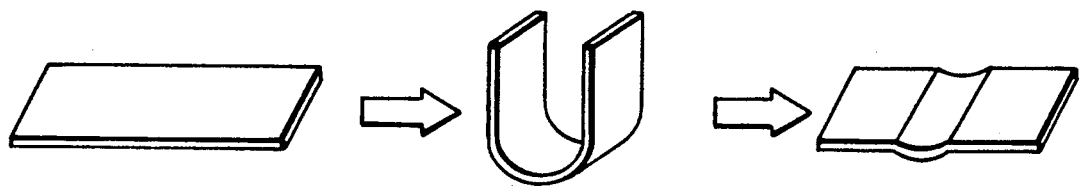
FIG. 8 is a diagrammatical sketch illustrating how to test of powdering property.

First, galvannealed steel sheets—having coating weight about 45 g/m² and processed in the galvannealing furnace on a constant line speed of 100 m/min but ar varied base steel temperatures of 480° C, 520° c. and 600° c.—were measured at their centers for their X-ray diffraction profiles. In FIG. 6, the X-ray diffraction profiles of the galvannealed coating processed at the base steel temperatures of 480° c., 520° c. and 600° c. in the galvannealing furnace are shown at 34, 35 and 36, respectively. It is found that variations in the sheet temperature in the galvannealing furnace give rise to changes in the X-ray diffraction intensities and the apex positions of the X-ray diffraction peaks of $\zeta$, $\delta_1$ and $\Gamma$ phases. The X-ray diffraction profiles shown in FIG. 6 were obtained at the step angle of 0.2° for the measuring time of 1 second, but the time needed for measurement was only 50 seconds. However, it takes 170 seconds to obtain X-ray diffraction profiles within the same $2\theta$ range as in FIG. 6 by driving a single detector.

With the system according to the present invention, it is thus possible to obtain X-ray diffraction profiles within a time span about ⅓ shorter than required in using a single detector; it is possible to achieve an on-line determination of X-ray diffraction profiles within a much more reduced span of time.

If the scanning ranges of the respective detectors are limited to the $2\theta$ ranges of the X-ray diffraction peaks of the $\zeta$, $\delta_1$ and $\Gamma$ phases, the measuring time can then be further decreased. For instance, a time span of as long as 50 seconds were needed for determining the X-ray diffraction profiles shown in FIG. 6, because the entire range of $2\theta = 121.5°-155.5°$ was covered. For measuring only the X-ray diffraction intensities at the apex positions of the X-ray diffraction peaks of the $\zeta$, $\delta_1$ and $\Gamma$ phases, the respective detectors may be driven within the following ranges.

For the detector to measure the X-ray diffraction intensity of the $\delta_1$ phase: $2\theta = 125.0°-129.0°$ (and $d = 1.29\text{Å}-1.27\text{Å}$).

For the detector to measure the X-ray diffraction intensity of the $\zeta$ phase: $2\theta = 129.0°-131.0°$ (and $d = 1.27\text{Å}-1.26\text{Å}$).

For the detector to measure the X-ray diffraction intensity of the $\Gamma$ phase: $2\theta = 138.0°-141.0°$ (and $d = 1.23\text{Å}-1.21\text{Å}$).

The time span needed for determining the X-ray diffraction intensities within the above-mentioned scanning ranges is 20 seconds.

Using galvannealed steel sheets varying in the degree of alloying, which have been produced by hot-dip galvanizing line at the base steel temperature in the galvannealing furnace and the coating weight, both said factors being varied within the above-mentioned ranges, investigation was then made of the relation between the estimating values of the $\zeta$ and $\Gamma$ phases and the drawing property and powdering property. The drawing property was estimated in terms of the outer diameter ratio in such a drawing test method as diagrammatically sketched in FIG. 7, in which the same lubricating oil was used. Conditions for drawing test:

Test piece

Diameter ($D_0$) of the disk (galvannealed steel sheet) before drawing: 75 mm

Thickness of the galvannealed steel sheet used for drawing: t mm

Mold

Diameter (d) of the punch used for drawings: 40 mm
Tip radius of the punch used for drawings: 5 mm
Radius of shoulder of the die for drawings: 5 tmm
Blank holder force applied at drawing: 1,000 kg Post-test state Drawn depth: 20 mm
Diameter of the flange after drawing: $D_1$ mm
Outer diameter ratio: $D_1/D_0$ The powdering property was estimated by such a powdering test method as sketched in FIG. 8. The conditions therefor are as follows: A test piece was subjected to a 180°-bending with the surface to be tested inside, thereby forming on that surface an curvature having a diameter six times as large as the thickness t of the test piece. After bending-back, a cellophane tape was affixed on the surface of the test piece, and then was peeled therefrom for visual evaluation of the amount of powder of coating metal deposited on that tape.

Rank 5: no powder was found
4: a slight amount of powder was found
3: a noticeable amount of powder was found
2: a large amount of powder was found
1: Release of much powder was taken place, even when no tape was used As to the press formability of the test piece, it was estimated good, when it came up to an outer diameter ratio of 0.745 or below in the drawing test and Rank 3 or more in the powdering test.

Table 1 shows results of drawing test and powdering test for two coils of galvannealed steel sheets produced under the same galvanizing and galvannealing conditions. The estimating values of the $\zeta$ and $\Gamma$ phase of one coil were found from the X-ray diffraction intensities thereof measured at the apex positions of the X-ray diffraction peaks by driving the detectors for scanning purposes, while those of another coil were determined from the X-ray diffraction intensities thereof measured by using the associated detectors fixed at the following positions.

For the detector to measure the X-ray diffraction intensity of the $\zeta$ phase: $2\theta = 130.3°$ (and $d = 1.26$ Å)

For the detector to measure the X-ray diffraction intensity of the $\Gamma$ phase: $2\theta = 139.0°$ (and $d = 1.22$ Å)

TABLE 1

| Example | Measuring Method | Coating Weight (g/m$^2$) | Estimating Value of $\zeta$ Phase | Estimating Value of $\Gamma$ Phase | Drawing Property (Outer Diameter Ratio) | Powdering Property | Formability |
|---|---|---|---|---|---|---|---|
| 1 | Scanning | 31 | 0.17 | 0.60 | 0.741 | 2 | Bad |
|   | Fixed | 31 | 0.15 | 0.39 | 0.741 | 2 | Bad |
| 2 | Scanning | 30 | 0.21 | 0.37 | 0.735 | 4 | Good |
|   | Fixed | 30 | 0.15 | 0.28 | 0.735 | 4 | Good |
| 3 | Scanning | 45 | 0.65 | 0.25 | 0.751 | 4 | Bad |
|   | Fixed | 45 | 0.34 | 0.23 | 0.751 | 4 | Bad |
| 4 | Scanning | 44 | 0.25 | 0.32 | 0.741 | 3 | Good |
|   | Fixed | 44 | 0.19 | 0.21 | 0.741 | 3 | Good |
| 5 | Scanning | 58 | 0.20 | 0.59 | 0.738 | 1 | Bad |
|   | Fixed | 58 | 0.16 | 0.39 | 0.738 | 1 | Bad |
| 6 | Scanning | 57 | 0.30 | 0.31 | 0.742 | 3 | Good |
|   | Fixed | 57 | 0.21 | 0.23 | 0.742 | 3 | Good |

Note: the term "scanning" refers to the results obtained by driving the $\zeta$ and $\Gamma$ phase detectors, and the term "fixed" refers to the results obtained by using the $\zeta$ and $\Gamma$ phase detectors fixed in place.

From Table 1, it is noted that in order to produce galvannealed steel sheets—which meets both the drawing property and the powdering property, the galvannealing may be carried out in such a method that the estimating values of the $\zeta$ and $\Gamma$ phases amount to about 0.35 or less and about 0.40 or less, respectively.

However, when the $\zeta$ and $\Gamma$ phase detectors are fixed at the above-mentioned positions, it is impossible to obtain accurate measurements of the X-ray diffraction intensities of the $\zeta$ and $\Gamma$ phases at the apex positions of the X-ray diffraction peaks; the estimating values of the $\zeta$ and $\Gamma$ phases are lower than those obtained by driving the associated detectors. Especially in the case of Examples Nos. 1, 3 and 5 wherein the detectors are fixed in place, the estimating values of the $\zeta$ and $\Gamma$ phases lie within the above-mentioned appropriate ranges, say, 0.35 or less and 0.40 or less, respectively, irrespective of a deterioration of press formability.

According to the system of this invention wherein, as herein disclosed in detail, detectors for detecting the X-ray diffraction intensities of the $\zeta$ and $\Gamma$ phase as well as the background intensity, preferably together with a detector for detecting the X-ray diffraction intensity of the $\delta_1$ phase, are independently provided for scanning purpose, it is possible to measure the X-ray diffraction intensities of the $\zeta$ and $\Gamma$ phases of galvannealed steel sheet—heat-treated (for alloying) just after—at the apex positions of the X-ray diffraction peaks and measure the X-ray diffraction intensity of the $\delta_1$ phase at the apex position of the X-ray diffraction peak, if the detector for detecting the X-ray diffraction intensity of the $\delta_1$ phase is additionally provided; it is possible to make an on-line, non-destructive and continuous determination of the press formability, of the galvannealed steel sheets with improved accuracy. Thus, the degree of alloying measured with the this system back to the heat-treating (alloying) conditions can be immediately fed back to the heat-treating (alloying) conditions to place them under appropriate control, whereby the galvannealed steel sheets improved in terms of quality can be stably produced without causing quality change in the line direction of the galvannealed steel sheets. This implies that any outgoing inspection can be dispensed with, contributing to energy-saving, production cost reductions, etc. Also, it is possible to achieve a rapid and simple determination of the degree of alloying of existing galvannealed steel sheets. The present invention is, therefore, of great industrial value.

What is claimed is:

1. A system for making an on-line determination of the degree of alloying in galvannealed steel sheets is characterized by including an X-ray tube for generating incident X-ray, two detectors for measuring the X-ray diffraction intensities of the $\zeta$ phase and $\Gamma$ phase in Fe-Zn respectively intermetallic compounds of said galvannealed coating and a detector for measuring the background intensity, all said detectors and X-ray tube being located on the same plane on the surface of galvannealed steel sheets, and further including an arithmetic unit for calculating results of the X-ray diffraction intensities.

2. A system as claimed in claim 1, wherein said detector for measuring the X-ray diffraction intensity of the $\zeta$ phase, said detector for measuring the X-ray diffraction intensity of the $\Gamma$ phase and said detector for measuring the background intensity are independently or simultaneously driven within the respective interplanar spacing ranges of $d = 1.30\text{Å}-1.23\text{Å}$, $d = 1.25\text{Å}-1.20\text{Å}$ and $1.20\text{Å}-1.17\text{Å}$ and on a circumference whose center is defined by the point of intersection of said incident X-ray with said galvannealed steel sheets.

3. A system as claimed in claim 1, further including a detector located on the same plane on the surface of said galvannealed steel sheets for measuring the X-ray diffraction intensity of the $\delta_1$ phase, said X-ray diffraction intensity being input to said arithmetic unit.

4. A system as claimed in claim 3, wherein said detector for detecting the X-ray diffraction intensity of the $\delta_1$ phase is driven independently, or simultaneously with the first-mentioned three detectors, within the interplanar spacing range of $d = 1.32\text{Å}-1.25\text{Å}$ and on a circumference whose center is defined by the point of intersection of said incident X-ray with galvannealed steel sheets.

* * * * *